(12) United States Patent
Gowda et al.

(10) Patent No.: US 9,375,504 B2
(45) Date of Patent: Jun. 28, 2016

(54) METHOD AND APPARATUS FOR FLUID STERILIZATION FOR PATIENT SUPPORT SURFACES

(71) Applicant: KAP Medical, Corona, CA (US)

(72) Inventors: Raj K. Gowda, Corona, CA (US); Dan F. Rosenmayer, Corona, CA (US)

(73) Assignee: KAP MEDICAL, INC., Corona, CA (US)

( * ) Notice: Subject to any disclaimer, the term of this patent is extended or adjusted under 35 U.S.C. 154(b) by 105 days.

(21) Appl. No.: 14/193,789

(22) Filed: Feb. 28, 2014

(65) Prior Publication Data

US 2014/0271349 A1 Sep. 18, 2014

Related U.S. Application Data

(60) Provisional application No. 61/791,792, filed on Mar. 15, 2013.

(51) Int. Cl.
*A61N 5/00* (2006.01)
*A61L 9/20* (2006.01)

(52) U.S. Cl.
CPC ............. *A61L 9/20* (2013.01); *A61L 2209/111* (2013.01)

(58) Field of Classification Search
CPC .............. A61L 9/00; A61L 9/032; A61L 9/18
USPC .............................. 422/24; 250/453.11, 492.1
See application file for complete search history.

(56) References Cited

U.S. PATENT DOCUMENTS

| 3,789,228 A * | 1/1974 | Bouchard ................ F24F 3/16 |
| | | 250/436 |
| 7,520,978 B2 | 4/2009 | Harbers |
| 2005/0125905 A1 | 6/2005 | Wilkinson |
| 2008/0199353 A1 | 8/2008 | Mlodzinski et al. |

FOREIGN PATENT DOCUMENTS

WO 2012/045111 4/2012

OTHER PUBLICATIONS

International Search Report and Written Opinion of the International Searching Authority for PCT/US2014/019463, mailed Jun. 26, 2014, 8 pages.
International Preliminary Report on Patentability mailed Sep. 15, 2015 from the International Bureau in related International Application No. PCT/US2014/019463.

* cited by examiner

*Primary Examiner* — Monzer R Chorbaji
(74) *Attorney, Agent, or Firm* — Faegre Baker Daniels LLP (57) ABSTRACT

An apparatus and method is provided for treating fluid provided to a patient support. An apparatus comprises a housing defining an interior space, an inlet in flow communication with a source of untreated fluid and the interior space, an outlet in flow communication with the patient support and the interior space, and a light source directed into the interior space such that light emitted by the light source bombards fluid flowing through the interior space with light within a wavelength range that destroys organisms within the fluid to thereby provide treated fluid to the patient support.

21 Claims, 6 Drawing Sheets

METHOD AND APPARATUS FOR FLUID STERILIZATION FOR PATIENT SUPPORT SURFACES

RELATED APPLICATION

This application claims the benefit of U.S. Provisional Patent Application Ser. No. 61/791,792, filed Mar. 15, 2014, titled METHOD AND APPARATUS FOR FLUID STERILIZATION FOR PATIENT SUPPORT SURFACES, docket KAPM0107(000006)-US, the entire disclosure of which is expressly incorporated by reference herein.

FIELD

The disclosure relates in general to patient supports and, more particularly, to a method and apparatus for fluid sterilization for patient supports surfaces.

BACKGROUND

Patient support surfaces are known. These support surfaces are inflated at least in part using air or other fluid. Such fluids may include impurities and/or organisms such as mold spores, fungi, bacteria and viruses. It is undesirable to place patients in close proximity to such impurities and/or organisms as they may cause infection and/or illness, aggravate allergies and create undesirable odors.

Accordingly, it is desirable to provide an apparatus for sterilizing fluid for use in patient support surfaces that overcomes one or more of the aforementioned drawbacks or other limitations of the prior art.

BRIEF DESCRIPTION OF THE DRAWINGS

The above-mentioned and other features and advantages of this disclosure, and the manner of attaining them, will become more apparent and the disclosure itself will be better understood by reference to the following description of embodiments taken in conjunction with the accompanying drawings, wherein:

FIGS. 1(*a*)-(*c*) illustrate conceptual views of various orientations of a UV chamber according to the present disclosure relative to a fluid inlet, a blower device, and a patient support;

Corresponding reference characters indicate corresponding parts throughout the several views. The exemplifications set out herein illustrate exemplary embodiments of the disclosure and such exemplifications are not to be construed as limiting the scope of the disclosure in any manner.

DETAILED DESCRIPTION OF THE DRAWINGS

The embodiments disclosed herein are not intended to be exhaustive or to limit the disclosure to the precise forms disclosed in the following detailed description. Rather, the embodiments are chosen and described so that others skilled in the art may utilize their teachings.

In an exemplary embodiment of the present disclosure an apparatus for treating fluid provided to a patient support is provided. The apparatus comprises a housing defining an interior space; an inlet in flow communication with a source of untreated fluid and the interior space; an outlet in flow communication with the patient support and the interior space; and a light source directed into the interior space such that light emitted by the light source bombards fluid flowing through the interior space with light within a wavelength range that destroys organisms within the fluid to thereby provide treated fluid to the patient support. In one example, the apparatus further comprises an opening into the interior space and a cover configured to cover the opening, the light source being mounted to the cover. In another example, the light source is a UVC LED and the wavelength range is between 255 nm and 285 nm. In a variation thereof, the UVC LED emits light at a wavelength of approximately 280 nm. In another example, the apparatus further comprises a microcontroller configured to receive a flow sensor signal indicating whether fluid is flowing through the interior space, the microcontroller outputting a control signal that causes deactivation of the light source when the flow sensor signal indicates that fluid is not flowing through the interior space. In a variation thereof, the apparatus further comprises an opening into the interior space, a cover configured to cover the opening, the light source being mounted to the cover, and a sensor mounted to the cover, the sensor being configured to provide to enable logic a first signal when the cover covers the opening to the interior space and a second signal when the cover does not cover the opening, the enable logic causing activation of the light source upon receipt of both the control signal from the microprocessor and the first signal from the sensor. In a further variation, the sensor comprises a Hall Effect sensor mounted to the cover and a magnet mounted to the housing at a location proximate to the Hall Effect sensor when the cover is attached to the housing to cover the opening to the interior space. In yet another example, the housing is mounted within a valve assembly configured to route fluid from the fluid source to the patient support.

In another embodiment of the present disclosure, a patient support system is provided, comprising: a patient support having an air inlet for receiving air to at least partially inflate the patient support; and a UV chamber having an inlet for receiving unsterilized air from an air source into an interior space of a housing, a light source that emits light toward the unsterilized air in the interior space at a wavelength that sterilizes the air, and an outlet in flow communication with the patient support inlet to provide sterilized air to the patient support. In one example, the patient support is one of a wheel chair cushion, a mattress, an overlay pad, a chair cushion, a chair pad, and a dialysis chair. In another example, the housing comprises an opening into the interior space, the light source being positioned to emit light through the opening. In a variation thereof, the UV chamber further comprises a removable cover that covers the opening when attached to the housing, the light source being mounted to the cover. In In yet a further variation, the cover further comprises a printed circuit board attached thereto having a first side with electronics mounted thereon and a second side with the light source mounted thereon. In still a further variation, the electronics include a microprocessor, enable logic connected to the microprocessor, a driver circuit connected between the enable logic and the light source, and a Hall Effect sensor connected to the enable logic. In a further variation, the microprocessor responds to an input that indicates air is flowing through the UV chamber by providing a control signal to the enable logic, the enable logic being configured to activate the driver circuit, which thereby activates the light source, upon receipt of both the control signal from the microprocessor and an input signal from Hall Effect sensor indicating that the cover is attached to the housing and covering the opening into the interior space. In another example, the the light source comprises a plurality of UVC LEDs. In another variation, the Hall Effect sensor is mounted to the printed circuit board such that when the cover covers the opening, the Hall Effect sensor is in close proximity to a magnet mounted to the housing.

In still another embodiment of the present disclosure, a method of sterilizing fluid for use in a patient support, comprising: passing unsterilized fluid from a fluid source through an inlet into an interior space of a chamber; emitting ultraviolet light toward the fluid in the interior space at a wavelength of between about 255 nm and about 285 nm to thereby sterilize the fluid; and passing the sterilized fluid through an outlet of the chamber to an inlet of a patient support to thereby at least partially inflate the patient support with sterilized fluid. In one example, the interior space is defined by a housing of the chamber, the housing having an opening, and the ultraviolet light is emitted toward the fluid through the opening. In a variation thereof, the method further comprises sensing whether a cover covers the housing opening, and discontinuing the emission of ultraviolet light upon sensing that the cover does not cover the opening. In another example, the emitting step comprises activating at least one UVC LED. In yet another example, the method further comprises sensing whether fluid is flowing through the interior space, and discontinuing the emission of ultraviolet light upon sensing that fluid is not flowing through the interior space.

As used herein, the term "support surface" refers to all support surfaces and immersion surfaces which support humans or animals and which are inflated at least in part, including, but not limited to wheel chair cushions, mattresses (including standard, bariatric, pediatric and neonatal), overlay pads, chair cushions, chair pads, and dialysis chairs. Additional details about such support surfaces are provided in U.S. Patent Application Ser. No. 61/713,856, filed on Oct. 15, 2012, titled PATIENT SUPPORT APPARATUS AND METHOD, the disclosure of which is expressly incorporated herein by reference.

Figure 1A:
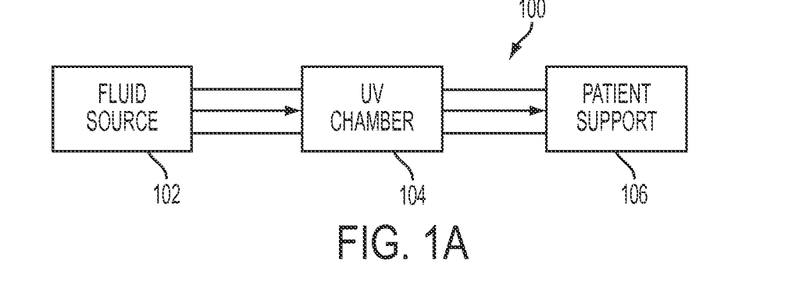

Referring now to the drawings, in its most basic form a system 100 according to the present disclosure generally includes a fluid source 102, a UV chamber 104 and a patient support 106 as depicted in FIG. 1(a). Fluid source 102 functions as a supply of air or other fluid in an untreated, unsterilized state. The fluid is then passed through UV chamber 104 where it is sterilized using ultra-violet technology as is further described below. The sterilized fluid is then passed to patient support 106 to inflate (or maintain a semi-inflated state of) patient support 106.

Figure 1B:
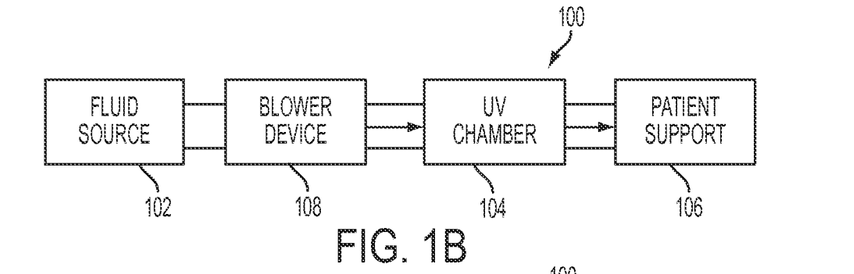
Figure 1C:
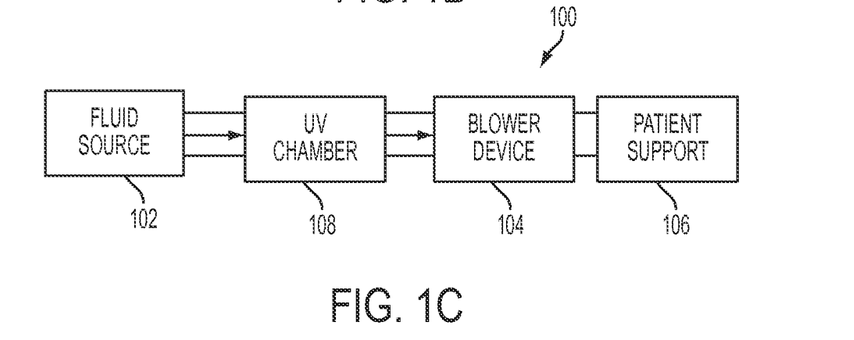

FIG. 1(b) is another generalized embodiment of system 100 wherein a blower device 108 such as a fan, compressor, or other device is used to force air from fluid source 102 through UV chamber 104 and into patient support 106. In FIG. 1(b), blower device 108 is situated upstream of UV chamber 104. In yet another embodiment as shown in FIG. 1(c), blower device 108 is situated downstream of UV chamber 104. In either case, blower device 104 forces unsterilized air through UV chamber 104 for sterilization prior to being provided to patient support 106.

In any of the above-mentioned embodiments, UV chamber 104 may be positioned within an existing valve assembly of the fluid supply circuit for the patient support 106 and coupled to the valve assembly electronics in the manner described below. More specifically, referring to FIG. 2, valve assembly 200 generally includes a housing 202, an inlet 204 and an outlet 206. Inlet 204 is in fluid communication with fluid source 102 (FIGS. 1(a), (c)) or blower device 108 (FIG. 1(b)) and outlet 206 is in fluid communication with patient support 106 (FIGS. 1(a)-(b)) or blower device 104 (FIG. 1(c)). Valve assembly 200 further includes control and power circuitry 208, which includes, among other things, a flow sensor 210 and a connector 212.

Figure 2:
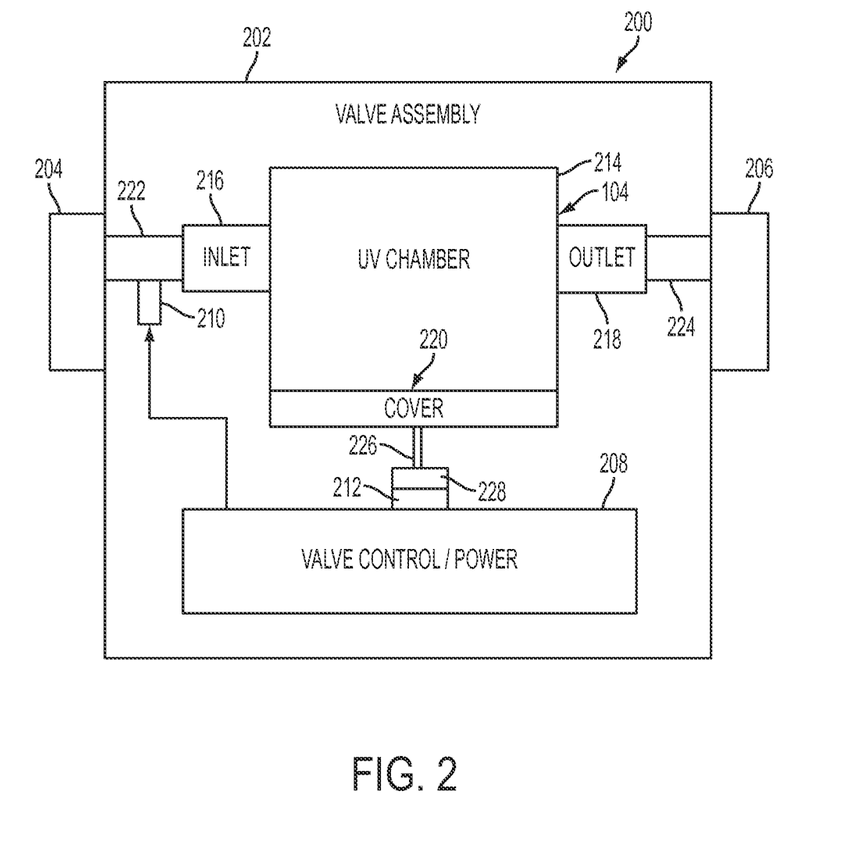
FIG. 2 is a conceptual view of a UV chamber according to the present disclosure mounted within a valve assembly.

UV chamber 104 generally includes a housing 214, an inlet 216, an outlet 218 and a cover 220. Inlet 216 is in fluid communication with valve assembly inlet 204 via conduit 222. Outlet 218 is in fluid communication with valve assembly outlet 206 via conduit 224. Cover 220 includes a printed circuit board and electronics as described below, which receive power from and are in communication with valve control and power circuitry 208. Specifically, a cable 226 is connected to cover 220 and a connector 228, which mates with connector 212 of valve control and power circuitry 208.

Figure 3:
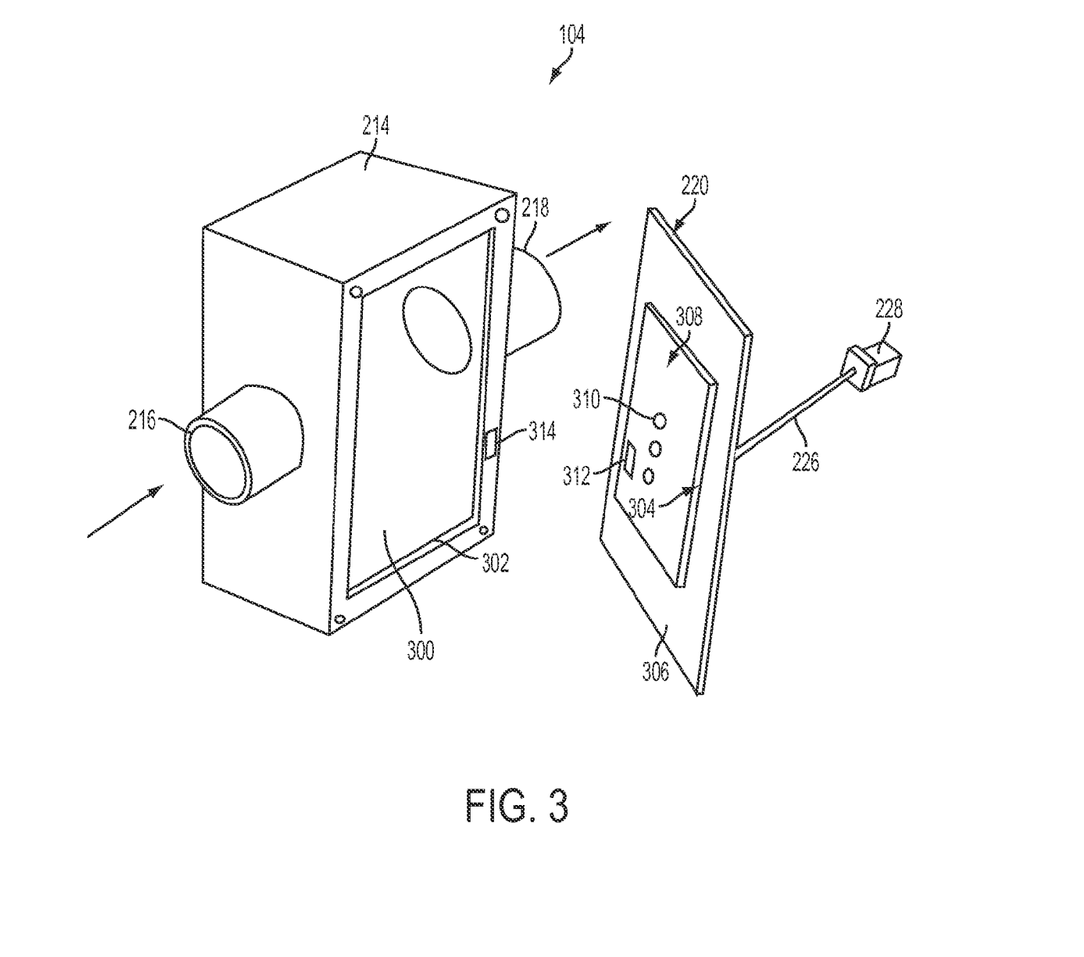
FIG. 3 is a perspective view of a UV chamber according to the present disclosure.

UV chamber 104 is shown in more detail in FIG. 3. As shown, housing 214 defines an interior space 300 which is in flow communication with inlet 216 and outlet 218. Housing 214 also includes an opening 302. When attached to housing 214, cover 220 entirely covers opening 302. Cover 220 includes a printed circuit board ("PCB") 304, which is mounted to an interior side 306 of cover 220 using standoffs or other conventional mounting techniques. In one embodiment, PCB 304 is a standard, double sided FR4, 0.062 inch copper clad PCB. Electronics 308 are mounted to the top side of PCB 304 (i.e., facing interior side 306 of cover 220) and connected to cable 226 and connector 228 as is further described below. PCB 304 also includes at least one UV light source 310 (three shown), which is mounted to the bottom side of PCB 304. In one embodiment of the disclosure, light source 310 is a UVC LED as is further described below. More or fewer than three light sources 310 may be used. When cover 220 is attached to housing 214 (using screws or other conventional fastening techniques), the bottom side of PCB 304 and more particularly light sources 310 are directed toward interior space 300. As should be apparent from the foregoing, light sources 310 may thereby sterilize the fluid flowing through UV chamber 104.

In one embodiment of the present disclosure, light sources 310 are ultraviolet C wavelength LEDs, which are LEDs that emit ultraviolet light in the sub range of wavelengths from 100 nm to 290 nm. Light sources 310 may be LEDs, tubes, bulbs or a combination thereof. In one embodiment, light sources 310 emit ultraviolet light having wavelengths of between 255 nm and 285 nm, or more specifically at a wavelength of about 280 nm. Light sources 310 emitting this wavelength have demonstrated the result of providing sterilization of almost any surface or media. In the present disclosure, light sources 310 bombard the potentially germ-laden fluid flowing through UV chamber 104 with ultraviolet C light and viruses, bacteria and mold spores are destroyed. All of the fluid (e.g., air) provided to patient support 106 will be purified or processed in this manner. By processing the fluid provided to patient support 106 with light sources 310, UV chamber 104 reduces the spread of airborne germs and other contaminants, kills odors, and provides a filterless, quiet, energy efficient fluid processing system.

It should be understood that the fluid provided to patient support 106 may be purified or processed by light sources 310 at any point upstream of patient support 106, and the depicted embodiments are only examples. In any such embodiment, however, all or substantially all of the fluid passed to patient support 10 should be passed through UV chamber 104 such that all or substantially all of the fluid passed through UV chamber 104 is passed under light sources 310.

It should be further understood that housing 214, while shown as a substantially rectangular enclosure in FIG. 3, may be formed in any of a variety of shapes which permit the flow of fluid between inlet 216 and outlet 218. For example, housing 214 may be formed such that the passage between inlet 216 and outlet 218 is reduced in any dimension shown, or is curved or cylindrical, or formed as a conduit between inlet 216 and outlet 218 in any appropriate shape. Moreover, UV chamber 104 may be disposed inside patient support 106 or outside patient support 106 as depicted in the figures described above.

Figure 4:
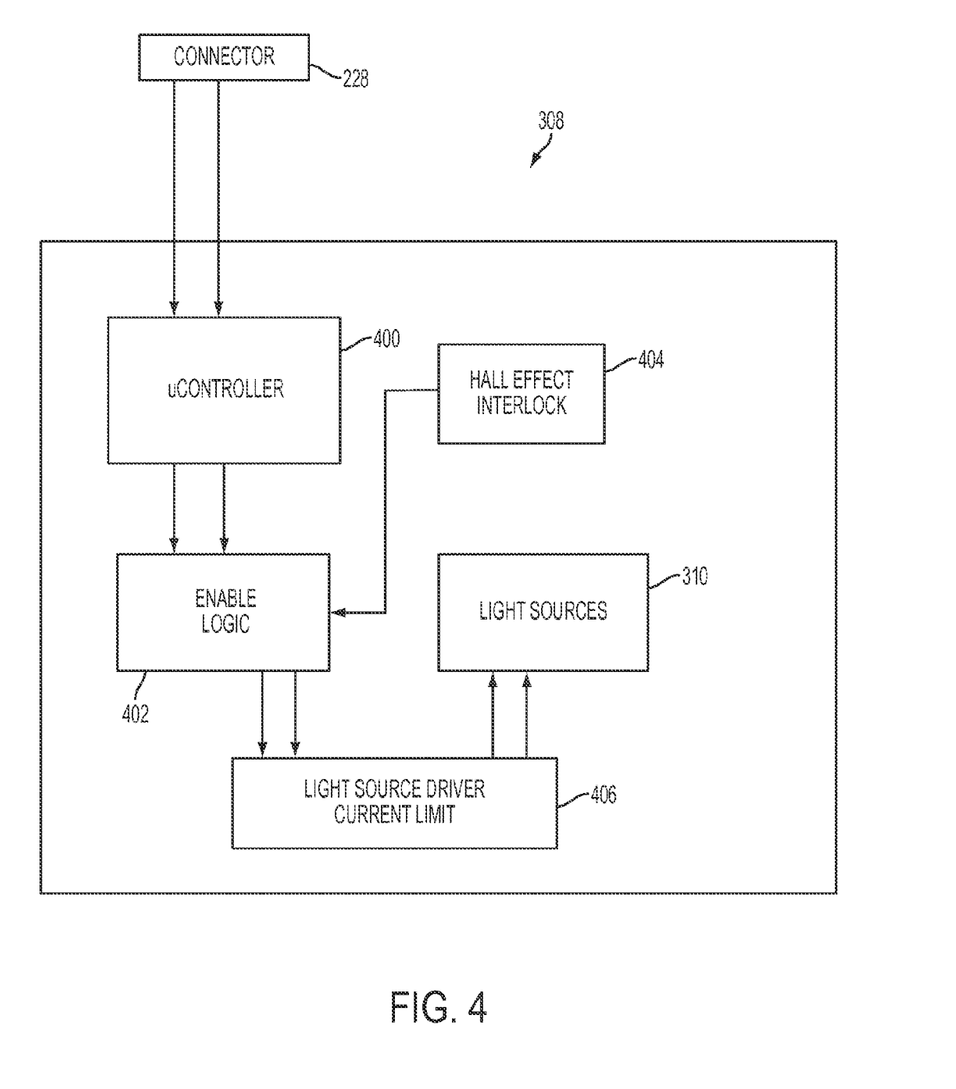
FIG. 4 is a block diagram of the electronics of the UV chamber of FIG. 3.

Referring now to FIG. 4, electronics 308 of PCB 304 generally include a microcontroller 400, enable logic 402, a Hall Effect interlock 404, a light source driver/current limit circuit 406 and light sources 310. In one embodiment, microcontroller 400 is the PIC18F13K22-I/55 device manufactured by Microchip. Microcontroller 400 is connected to connector 228, which provides power, ground and control signals from valve control/power circuitry 208 to electronics 308. Microcontroller 400 provides control signals to enable logic 402 to control light sources 310 in the manner described below. Enable logic 402 provides control signals to circuit 406 based on the control signals from microcontroller 400 and an input signal from Hall Effect interlock 404. As such, depending upon the signals provided to enable logic 402, circuit 406 either activates or deactivates light sources 310 and limits the current provided to light sources 310 to approximately 20 mA.

Referring back to FIG. 3, Hall Effect interlock 404 includes a Hall Effect sensor 312 mounted to PCB 304 and a magnet 314 mounted to housing 214. When cover 220 is attached to housing 214 and covering opening 302, sensor 312 is in close proximity to magnet 314, and therefore provides a signal to enable logic 402 indicating that UV chamber 104 is closed. When cover 220 is removed from housing 214 or no longer covers opening 302, sensor 312 provides a different signal to enable logic 402 indicating that UV chamber 104 is opened. It should be understood that while Hall Effect sensor 312 is described herein, any of a variety of different sensing technologies may be used to provide signals to enable logic 402 indicating whether UV chamber 104 is opened or closed. For example, a switch could be attached to cover 220 such that it is mechanically toggled when cover 220 is removed from opening 302. Alternatively, cover 220 could include an optical sensor, an IR sensor, or other suitable sensor that switches from one state to another when cover 220 is removed from opening 302.

As is described below, enable logic 402 uses the signals from Hall Effect interlock 404 to ensure that light sources 310 are deactivated whenever cover 220 is removed from opening 302. Additionally, enable logic 402 deactivates light sources 310 when fluid is not flowing through UV chamber 104 as indicated by flow sensor 210 (FIG. 2). A flowchart depicting a control loop 500 implemented by electronics 308 for controlling the activation of light sources 310 is provided in FIG. 5. Unless activated by control loop 500, light sources 310 are by default deactivated. At block 502, it is determined whether fluid is being provided to patient support 106 (i.e., whether fluid is flowing through UV chamber 104). In the implementation of FIG. 2, this determination is made based on the signal provided by flow sensor 210. If fluid is flowing through conduit 222, flow sensor 210 provides a signal to circuitry 208 indicating such flow. Circuitry 208 in turn provides a signal through connectors 212 and 228 and cable 226 to electronics 308 on PCB 304. Specifically, this signal is provided to microcontroller 400, which provides a control signal to enable logic 402 indicating that fluid is flowing through UV chamber 104. If fluid is not flowing, flow sensor 210 provides a different signal to circuitry 208, which causes microprocessor 400 to provide a different control signal to enable logic 402. If the determination at block 502 is that fluid is not flowing, then control loop 500 continues to monitor the status of fluid flow and light sources 310 remain deactivated.

Figure 5:
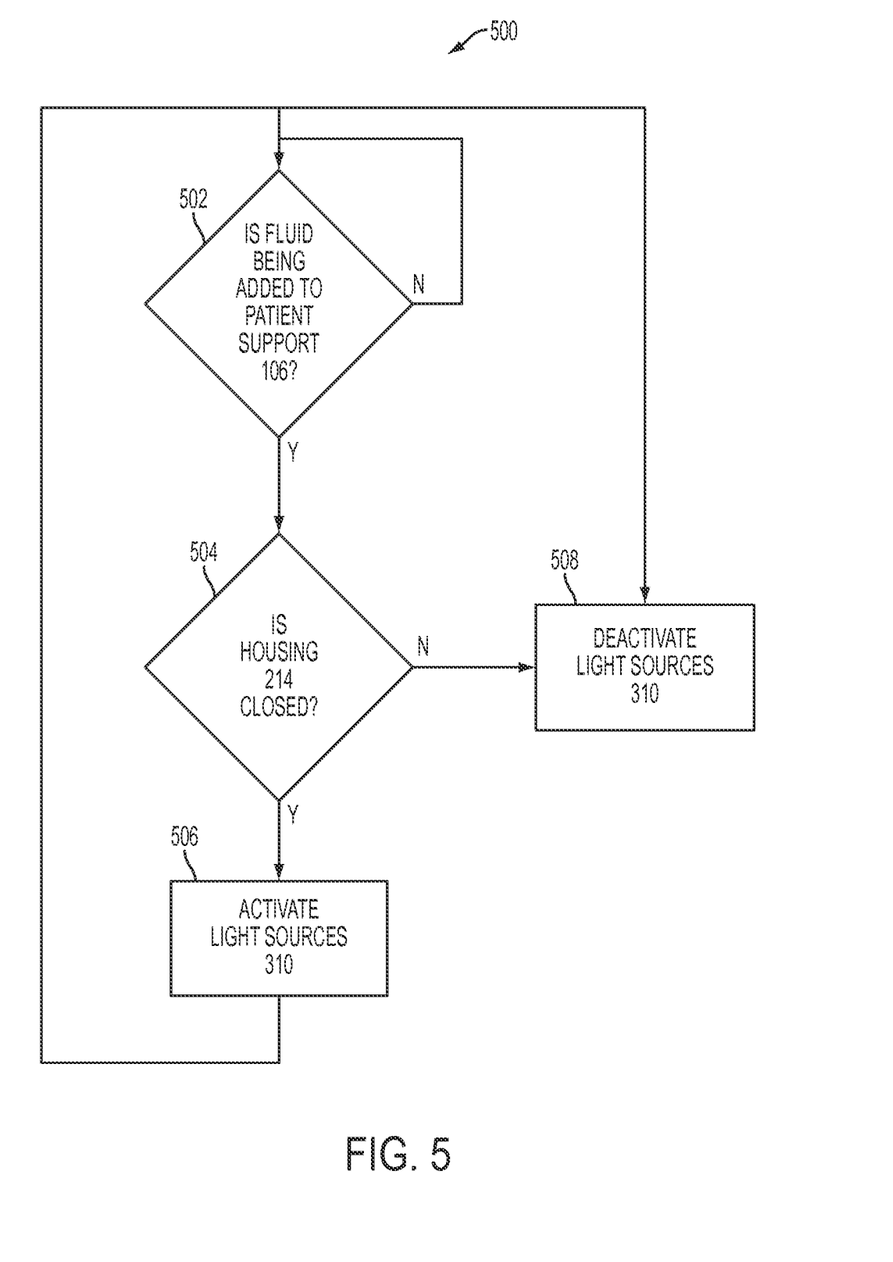
FIG. 5 is a flowchart of a control loop implemented by the electronics of FIG. 4.

If, on the other hand, it is determined at block 502 that fluid is flowing through UV chamber 104, then the determination is made at block 504 whether housing 214 is closed. More specifically, Hall Effect interlock 404 provides one input to enable logic 402 if cover 220 is covering opening 302 and another input to enable logic 402 if cover 220 is not covering opening 302. This input causes enable logic 402 to provide a control signal to light source driver/current limit circuit 406 to enable light sources 310 (block 506) if cover 220 is in place (i.e., housing 214 is closed) and to disable light sources 310 (block 508) if cover 220 is not in place (i.e., housing 214 is opened). It should be noted that interlock 404 operates independently of microprocessor 400, and therefore functions to prevent activation of light sources 310 even in the event that microprocessor 400 malfunctions. As such, control loop 500 enables light sources 310 only if fluid is flowing through UV chamber 104 and housing 214 is closed. Light sources 310 are disabled if either fluid is not flowing through housing 214 or housing 214 is opened.

Figure 6:
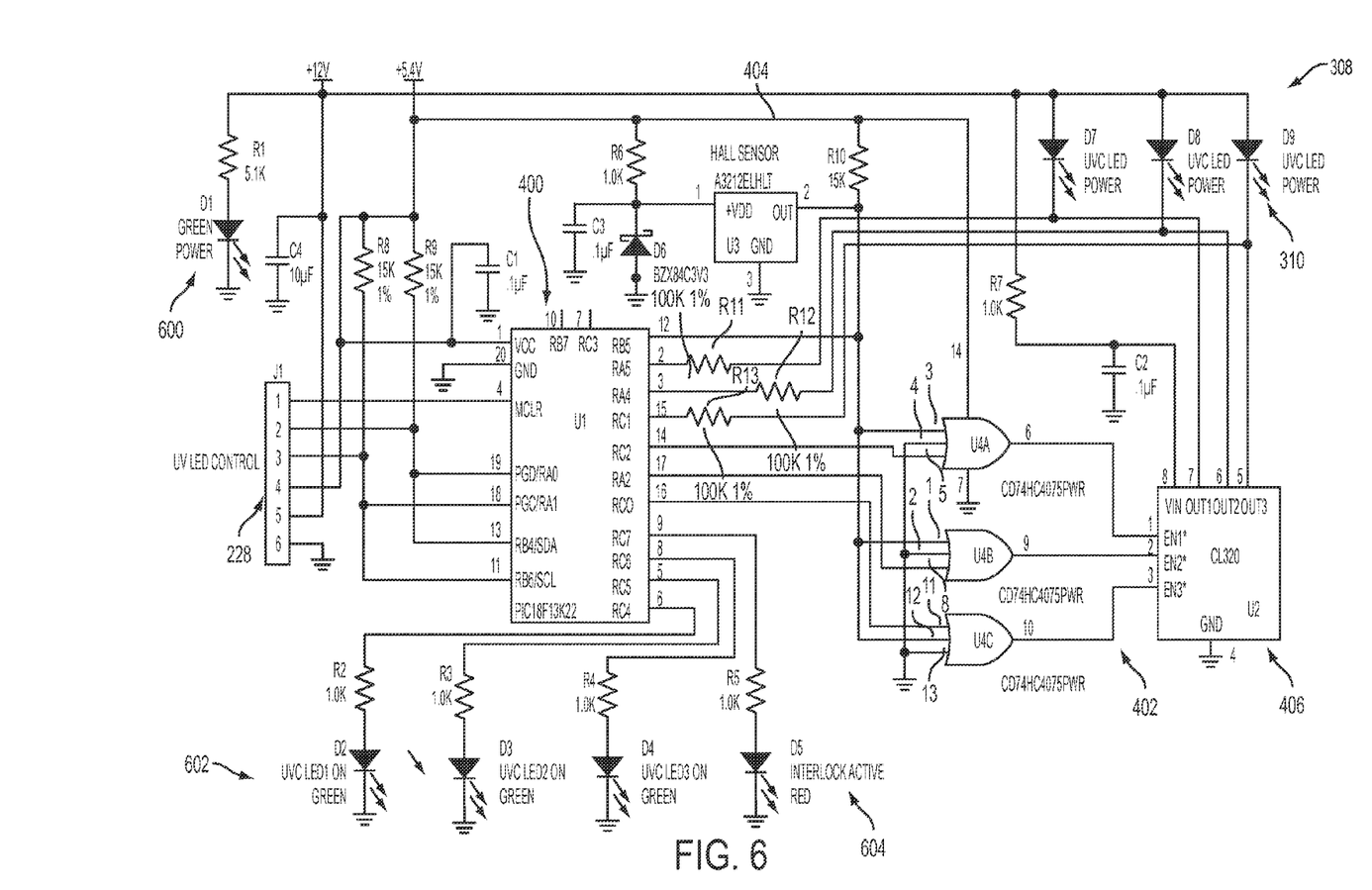
FIG. 6 is a schematic diagram of the electronics of FIG. 4.

FIG. 6 provides a schematic diagram of one implementation of the high level diagram of electronics 308 of FIG. 4 and control loop 500 of FIG. 5. As shown, in addition to the components depicted in FIG. 4, electronics 308 also includes a power indicator 600 which is mounted to housing 214 and activated when power is supplied to electronics 308, three light source activated indicators 602, a Hall Effect active indicator 604, and various passive components. The light source indicators 602 are also mounted to housing 214 and are activated when light sources 310 are activated, thereby providing a visual indication external to UV chamber 104 that light sources 310 are activated. Similarly, indicator 604 is mounted to housing 214 and activated when Hall Effect interlock 404 is activated (i.e., when cover 220 covers opening 302), thereby providing a visual indication external to UV chamber that interlock 404 is activated.

Depending upon how microcontroller 400 is programmed, each of light sources 310 may be activated individually and in a sequential order, or all of light sources 310 may be activated simultaneously. If one of the light sources 310 is sensed as being defective, microcontroller 400 may skip activation of that light source 310 if sequential activation is implemented.

While this disclosure includes particular examples, it is to be understood that the disclosure is not so limited. Numerous modifications, changes, variations, substitutions, and equivalents will occur to those skilled in the art without departing from the spirit and scope of the present disclosure upon a study of the drawings, the specification, and the following claims.

The invention claimed is:

1. An apparatus for treating fluid provided to a patient support, comprising:
   a housing defining an interior space;
   an opening into the interior space;
   an inlet in flow communication with a source of untreated fluid and the interior space;
   an outlet in flow communication with the patient support and the interior space;
   a light source directed into the interior space such that light emitted by the light source bombards fluid flowing through the interior space with light within a wavelength range that destroys organisms within the fluid to thereby provide treated fluid to the patient support; and
a cover configured to cover the opening, the light source being mounted to the cover.

2. The apparatus of claim 1, wherein the light source is a UVC LED and the wavelength range is between 255 nm and 285 nm.

3. The apparatus of claim 2, wherein the UVC LED emits light at a wavelength of approximately 280 nm.

4. An apparatus for treating fluid provided to a patient support, comprising:
a housing defining an interior space;
an inlet in flow communication with a source of untreated fluid and the interior space;
an outlet in flow communication with the patient support and the interior space.
a light source directed into the interior space such that light emitted by the light source bombards fluid flowing through the interior space with light within a wavelength range that destroys organisms within the fluid to thereby provide treated fluid to the patient support; and
a microcontroller configured to receive a flow sensor signal indicating whether fluid is flowing through the interior space, the microcontroller outputting a control signal that causes deactivation of the light source when the flow sensor signal indicates that fluid is not flowing through the interior space.

5. The apparatus of claim 4, further comprising:
an opening into the interior space, and
a cover configured to cover the opening, the light source being mounted to the cover, and a sensor mounted to the cover, the sensor being configured to provide to an enable logic a first signal when the cover covers the opening to the interior space and a second signal when the cover does not cover the opening, the enable logic causing activation of the light source upon receipt of both the control signal from the microprocessor and the first signal from the sensor.

6. The apparatus of claim 5, wherein the sensor comprises a Hall Effect sensor mounted to the cover and a magnet mounted to the housing at a location proximate to the Hall Effect sensor when the cover is attached to the housing to cover the opening to the interior space.

7. The apparatus of claim 4, wherein the light source is a UVC LED and the wavelength range is between 255 nm and 285 nm.

8. An apparatus for treating fluid provided to a patient support, comprising:
a housing defining an interior space;
an inlet in flow communication with a source of untreated fluid and the interior space;
an outlet in flow communication with the patient support and the interior space; and
a light source directed into the interior space such that light emitted by the light source bombards fluid flowing through the interior space with light within a wavelength range that destroys organisms within the fluid to thereby provide treated fluid to the patient support, wherein the housing is mounted within a valve assembly configured to route fluid from the fluid source to the patient support.

9. The apparatus of claim 8, wherein the light source is a UVC LED and the wavelength range is between 255 nm and 285 nm.

10. A patient support system, comprising:
a patient support having an air inlet for receiving air to at least partially inflate the patient support; and
a UV chamber having an inlet for receiving unsterilized air from an air source into an interior space of a housing, a light source that emits light toward the unsterilized air in the interior space at a wavelength that sterilizes the air, wherein the housing comprises an opening into the interior space, the light source being positioned to emit light through the opening, an outlet in flow communication with the patient support air inlet to provide sterilized air to the patient support and a removable cover that covers the opening when attached to the housing, the light source being mounted to the removable cover.

11. The system of claim 10, wherein the patient support is one of a wheel chair cushion, a mattress, an overlay pad, a chair cushion, a chair pad, and a dialysis chair.

12. The system of claim 10, wherein the removable cover further comprises a printed circuit board attached thereto having a first side with electronics mounted thereon and a second side with the light source mounted thereon.

13. The system of 12, wherein the electronics include a microprocessor, an enable logic connected to the microprocessor, a driver circuit connected between the enable logic and the light source, and a Hall Effect sensor connected to the enable logic.

14. The system of claim 13, wherein the microprocessor responds to an input that indicates air is flowing through the UV chamber by providing a control signal to the enable logic, the enable logic being configured to activate the driver circuit, which thereby activates the light source, upon receipt of both the control signal from the microprocessor and an input signal from Hall Effect sensor indicating that the removable cover is attached to the housing and covering the opening into the interior space.

15. The system of claim 13, wherein the Hall Effect sensor is mounted to the printed circuit board such that when the removable cover covers the opening, the Hall Effect sensor is in close proximity to a magnet mounted to the housing.

16. The system of claim 10, wherein the light source comprises a plurality of UVC LEDs.

17. The apparatus of claim 10, wherein the light source is a UVC LED and the wavelength range is between 255 nm and 285 nm.

18. A method of sterilizing fluid for use in a patient support, comprising:
passing unsterilized fluid from a fluid source through an inlet into an interior space of a chamber;
emitting ultraviolet light toward the fluid in the interior space at a wavelength of between about 255 nm and about 285 nm to thereby sterilize the fluid;
passing the sterilized fluid through an outlet of the chamber to an inlet of the patient support to thereby at least partially inflate the patient support with sterilized fluid; and
sensing whether fluid is flowing through the interior space, and discontinuing the emission of ultraviolet light upon sensing that fluid is not flowing through the interior space.

19. The method of claim 18, wherein the interior space is defined by a housing of the chamber, the housing having an opening, and the ultraviolet light is emitted toward the fluid through the opening.

20. The method of claim 18, wherein emitting comprises activating at least one UVC LED.

21. A method of sterilizing fluid for use in a patient support, comprising:
passing unsterilized fluid from a fluid source through an inlet into an interior space of a chamber;

emitting ultraviolet light toward the fluid in the interior space at a wavelength of between about 255 nm and about 285 nm to thereby sterilize the fluid, wherein the interior space is defined by a housing of the chamber, the housing having an opening, and the ultraviolet light is emitted toward the fluid through the opening;

passing the sterilized fluid through an outlet of the chamber to an inlet of the patient support to thereby at least partially inflate the patient support with sterilized fluid; and sensing whether a cover covers the housing opening, and discontinuing the emission of ultraviolet light upon sensing that the cover does not cover the opening.

\* \* \* \* \*